United States Patent
Emken et al.

(10) Patent No.: US 10,064,573 B2
(45) Date of Patent: *Sep. 4, 2018

(54) ANALYTE PERMEABLE MEMBRANE SYSTEMS FOR OXIDATIVE AND OPTICAL STABILITY

(71) Applicant: Senseonics, Incorporated, Germantown, MD (US)

(72) Inventors: Jeremy Emken, Germantown, MD (US); Philip Huffstetler, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 79 days.

This patent is subject to a terminal disclaimer.

(21) Appl. No.: 15/250,087

(22) Filed: Aug. 29, 2016

(65) Prior Publication Data

US 2017/0049371 A1   Feb. 23, 2017

Related U.S. Application Data

(63) Continuation of application No. 14/142,017, filed on Dec. 27, 2013, now Pat. No. 9,427,182.

(Continued)

(51) Int. Cl.
*A61B 5/1455* (2006.01)
*A61B 5/1459* (2006.01)

(Continued)

(52) U.S. Cl.
CPC ........ *A61B 5/14532* (2013.01); *A61B 5/0031* (2013.01); *A61B 5/1459* (2013.01); *A61B 2562/162* (2013.01)

(58) Field of Classification Search
CPC . A61B 5/1455; A61B 5/1459; A61B 5/14532; A61B 5/6867

See application file for complete search history.

(56) References Cited

U.S. PATENT DOCUMENTS 4,925,268 A    5/1990  Iyer et al.
6,330,464 B1  12/2001  Colvin, Jr. et al.
(Continued)

FOREIGN PATENT DOCUMENTS

CN    1658902 A    8/2005
CN    1942764 A    4/2007
(Continued)

*Primary Examiner* — Eric Winakur
(74) *Attorney, Agent, or Firm* — Rothwell, Figg, Ernst & Manbeck, P.C.

(57) ABSTRACT

A sensor that may be used to detect the presence, amount, and/or concentration of an analyte in a medium within an animal. The sensor may include a sensor housing, an indicator element embedded within and/or covering at least a portion of the sensor housing, and a membrane over the indicator element. The membrane may reduce indicator element deterioration by preventing immune cells, such as white blood cells, from contacting the indicator element, substantially prevent transmission of light of at least a specified wavelength or range of wavelengths through the membrane, and/or permit the analyte to pass through to the indicator element. The membrane may be an opaque diffusion membrane. The sensor may include a foil. The foil may block light and/or reduce indicator element deterioration. The membrane may reduce oxidation of the indicator element.

25 Claims, 12 Drawing Sheets

Related U.S. Application Data

(60) Provisional application No. 61/746,790, filed on Dec. 28, 2012, provisional application No. 61/847,881, filed on Jul. 18, 2013.

(51) Int. Cl.
  *A61B 5/145* (2006.01)
  *A61B 5/00* (2006.01)

(56) References Cited

U.S. PATENT DOCUMENTS

| | | |
|---|---|---|
| 6,405,066 B1 | 6/2002 | Essenpreis et al. |
| 6,702,857 B2 | 3/2004 | Brauker et al. |
| 7,713,745 B2 | 5/2010 | Colvin, Jr. et al. |
| 8,126,554 B2 | 2/2012 | Kane et al. |
| 2004/0176672 A1 | 9/2004 | Silver et al. |
| 2005/0175702 A1 | 8/2005 | Muller-Schulte |
| 2007/0235331 A1 | 10/2007 | Simpson et al. |
| 2009/0124875 A1 | 5/2009 | Bentsen et al. |
| 2011/0236989 A1 | 9/2011 | Suri et al. |
| 2012/0238842 A1 | 9/2012 | Colvin, Jr. et al. |

FOREIGN PATENT DOCUMENTS

| | | |
|---|---|---|
| WO | 2010/123972 A1 | 10/2010 |
| WO | 2014/043204 A1 | 3/2014 |

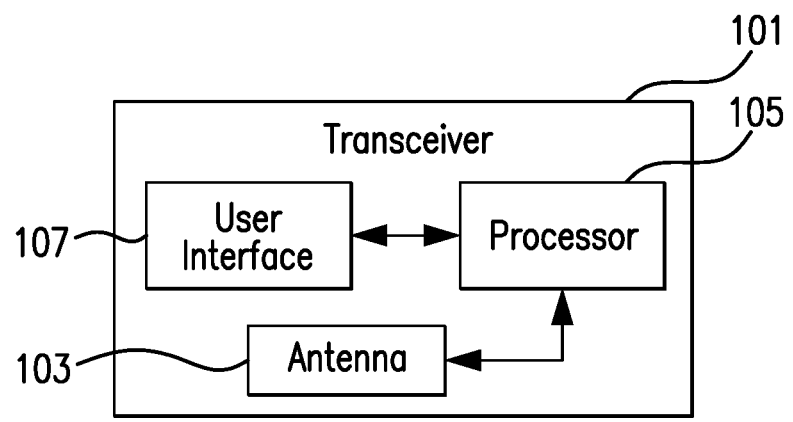
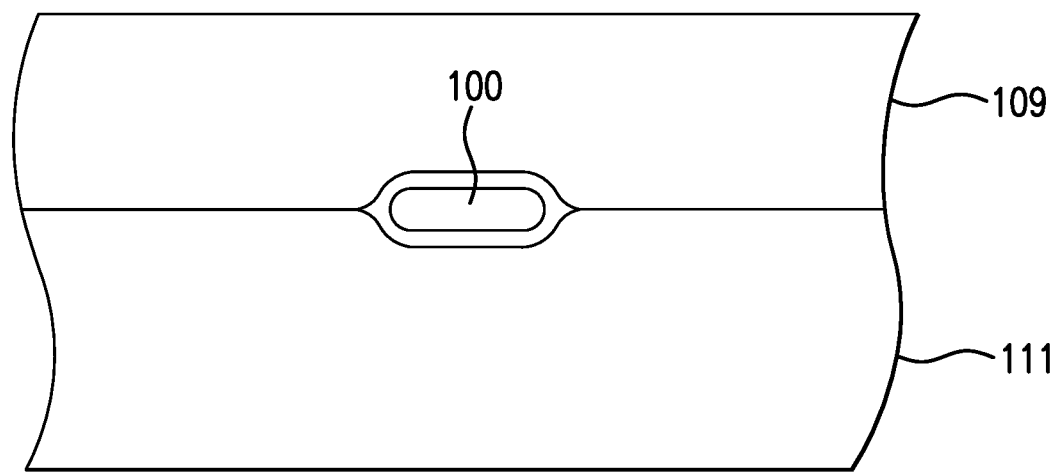
FIG. 1

ANALYTE PERMEABLE MEMBRANE SYSTEMS FOR OXIDATIVE AND OPTICAL STABILITY

CROSS-REFERENCE TO RELATED APPLICATIONS

This application is a continuation of U.S. patent application Ser. No. 14/142,017, filed on Dec. 27, 2013, which claims the benefit of priority to U.S. Provisional Application Ser. No. 61/746,790, filed on Dec. 28, 2012, and U.S. Provisional Application Ser. No. 61/847,881, filed on Jul. 18, 2013, all of which are incorporated herein by reference in their entireties.

BACKGROUND

Field of Invention

The present invention relates generally to sensors for implantation or insertion within a living animal and measurement of a concentration of an analyte in a medium within the living animal. Specifically, the present invention relates to sensors having a membrane over an indicator element on the surface of the sensor body.

Discussion of the Background

A sensor may include an indicator element, such as, for example, indicator molecules embedded or polymerized in or onto a polymer graft (i.e., layer or matrix). For example, in an implantable fluorescence-based glucose sensor, fluorescent indicator molecules may reversibly bind glucose and, when illuminated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system begins to attack the sensor. For instance, if a sensor is implanted in a human, white blood cells attack the sensor as a foreign body, and, in the initial immune system onslaught, neutrophils are the primary white blood cells attacking the sensor. Macrophages and giant cells may further attack the sensor. The defense mechanism of neutrophils and other white blood cells includes the release of highly oxidative substances known as reactive oxygen species (ROS), such as hydrogen peroxide ($H_2O_2$), hydroxyl radical ($OH^\bullet$), hypochlorite ($OCl^-$), peroxynitrite ($OONO^-$), and superoxide ($O_2^-$).

ROS, such as hydrogen peroxide, may degrade indicator molecules. For instance, in indicator molecules having a boronate group, hydrogen peroxide may degrade the indicator molecules by oxidizing the boronate group, thus disabling the ability of the indicator molecule to bind glucose.

In addition, if the sensor is an optical sensor, light (e.g., excitation light, fluorescent light emitted by the indicator molecules) from the sensor may pass through the indicator element or other transparent portions of the sensor. If the sensor has been implanted in animal tissue, the light may be reflected by the tissue or may cause the tissue to fluoresce and return light at a different wavelength. The reflected and fluoresced light from the tissue may return through the indicator element or other transparent part of the sensor and may be received by one or more light detectors (e.g., photodiodes) of the sensor. This results in noise in the signals received by the light detectors.

Moreover, if the animal (e.g., a human patient) is in a brightly lit area, then the light may pass through the patient's skin and be received by the light detectors of the sensor. This could also introduce noise into the signals received by the light detectors. Thus, erroneous sensor readings may occur because light detectors in an implanted sensor may receive additional signals unrelated to the analyte concentration.

There is presently a need in the art for improvements in optical sensor isolation and reducing indicator element degradation.

SUMMARY

The present invention overcomes the disadvantages of prior systems by providing, among other advantages, improved optical isolation and/or reduced indicator element degradation while still allowing an analyte of interest to reach the indicator element.

One aspect of the present invention provides a sensor that may be used for in vivo detection of the presence, amount, and/or concentration of an analyte in a medium within a living animal. The sensor may include a sensor housing, an indicator element embedded within and/or covering at least a portion of the sensor housing, and a membrane over at least a portion of the indicator element. The indicator element may include indicator molecules.

In some embodiments, the membrane may have pores configured to substantially prevent white blood cells from passing through the membrane but to permit the analyte to pass through the membrane. The membrane may be opaque. In some embodiments, the membrane may catalyze degradation of ROS, such as hydrogen peroxide, and reduce deterioration of the indicator element. The membrane may comprise a hydrophilic or hydrophobic membrane material.

In some embodiments, the membrane is a porous, opaque diffusion membrane covering at least a portion of the housing and the graft, and the membrane may be configured to substantially prevent white blood cells from passing through the membrane and permit an analyte of interest to pass through the membrane to the indicator element and to substantially prevent transmission of light of at least a specified wavelength or range of wavelengths through the membrane. The diffusion membrane may comprise an opaque or light absorbing colorant.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 1 is a schematic view of a sensor system, which includes an implantable sensor and a sensor reader, embodying aspects of the present invention.

DETAILED DESCRIPTION OF PREFERRED EMBODIMENTS

Figure 2:
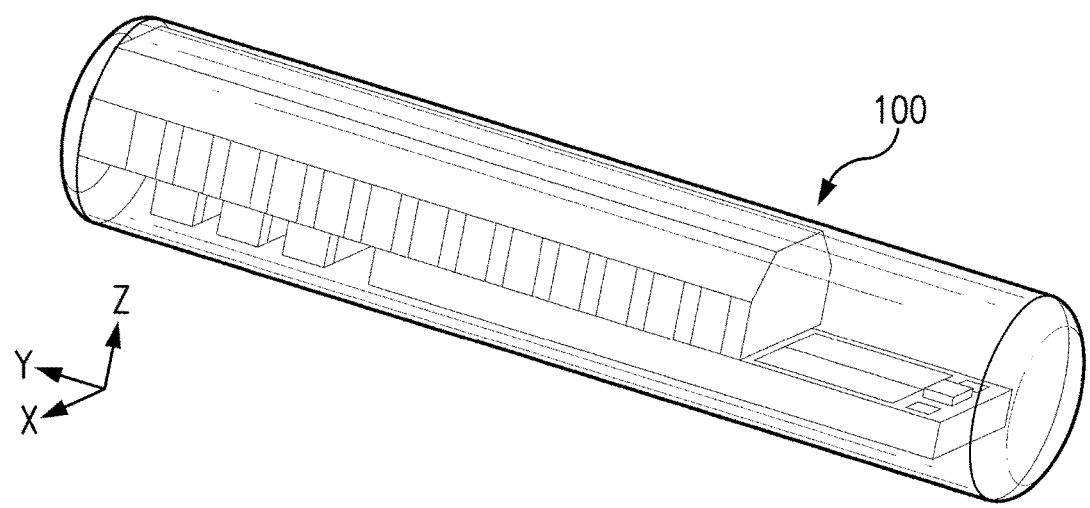
FIG. 2 illustrates a perspective view of a sensor embodying aspects of the present invention.

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting. All patents, applications, published applications, and other publications referred to herein are incorporated by reference in their entirety.

FIG. 1 is a schematic view of a sensor system embodying aspects of the present invention. In one non-limiting embodiment, the system includes a sensor 100 and an external transceiver 101. In the embodiment shown in FIG. 1, the sensor 100 is implanted in a living animal (e.g., a living human). The sensor 100 may be implanted, for example, in a living animal's arm, wrist, leg, abdomen, or other region of the living animal suitable for sensor implantation. For example, as shown in FIG. 1, in one non-limiting embodiment, the sensor 100 may be implanted between the skin 109 and subcutaneous tissues 111. In some embodiments, the sensor 100 may be an optical sensor. In some embodiments, the sensor 100 may be a chemical or biochemical sensor.

A transceiver 101 may be an electronic device that communicates with the sensor 100 to power the sensor 100 and/or obtain analyte (e.g., glucose) readings from the sensor 100. In non-limiting embodiments, the transceiver 101 may be a handheld reader, a wristwatch, waistband, or an armband. In other non-limiting embodiments, the transceiver 101 may be held on a user's body by adhesive (e.g., as part of a biocompatible patch). In one embodiment, positioning (i.e., hovering or swiping/waiving/passing) the transceiver 101 within range over the sensor implant site (i.e., within proximity of the sensor 100) will cause the transceiver 101 to automatically convey a measurement command to the sensor 100 and receive a reading from the sensor 100.

In some embodiments, the transceiver 101 may include an antenna 103, a processor 105 and/or a user interface 107. In one non-limiting embodiment, the user interface 107 may include a liquid crystal display (LCD), but, in other embodiments, different types of displays may be used.

In some embodiments, the antenna 103 may include an inductive element, such as, for example, a coil. The antenna 103 may generate an electromagnetic wave or electrodynamic field (e.g., by using a coil) to induce a current in an inductive element (e.g., inductive element 114 of FIGS. 3-8) of the sensor 100, which powers the sensor 100. The antenna 103 may also convey data (e.g., commands) to the sensor 100. For example, in a non-limiting embodiment, the antenna 103 may convey data by modulating the electromagnetic wave used to power the sensor 100 (e.g., by modulating the current flowing through a coil of the antenna 103). The modulation in the electromagnetic wave generated by the transceiver 101 may be detected/extracted by the sensor 100. Moreover, the antenna 103 may receive data (e.g., measurement information) from the sensor 100. For example, in a non-limiting embodiment, the antenna 103 may receive data by detecting modulations in the electromagnetic wave generated by the sensor 100, e.g., by detecting modulations in the current flowing through the coil of the antenna 103.

The inductive element of the antenna 103 and the inductive element (e.g., inductive element 114 of FIGS. 3-8) of the sensor 100 may be in any configuration that permits adequate field strength to be achieved when the two inductive elements are brought within adequate physical proximity.

In some embodiments, the processor 105 may calculate one or more analyte concentrations based on the analyte readings received from the sensor 100. In some embodiments, the processor 105 may also generate one or more alerts and/or alarms based on the calculated analyte concentrations (e.g., if the calculated analyte concentration exceeds or falls below one or more thresholds). The calculated analyte concentrations, alerts, and/or alarms may be displayed via the user interface 107.

In some embodiments, the transceiver 101 may communicate (e.g., using a wireless communication standard, such as, for example, Bluetooth) with a remote device (e.g., a smartphone, personal data assistant, handheld device, or laptop computer). The remote device may receive calculated analyte concentrations, alerts, and/or alarms from the transceiver 101 and display them. Display by the remote device may be in addition to, or in the alternative to, display by the user interface 107 of the transceiver 101. For example, in some embodiments, as illustrated in FIG. 1, the transceiver 101 may include a user interface 107, but this is not required. In some alternative embodiments, the transceiver 101 may not have a user interface 107, and calculated analyte concentrations, alerts, and/or alarms may instead be displayed by a remote device.

In some non-limiting embodiments, the transceiver 101 may have some or all of the structure described in U.S. patent application Ser. No. 13/937,871, which is incorporated herein by reference in its entirety, with particular reference to FIGS. 1 and 9.

FIGS. 2-8 illustrate a non-limiting embodiment of a sensor 100 embodying aspects of the present invention that may be used in the sensor system illustrated in FIG. 1. In some embodiments, the sensor 100 may be an optical sensor. In one non-limiting embodiment, sensor 100 includes a sensor housing 102 (i.e., body, shell, or capsule). In exemplary embodiments, sensor housing 102 may be formed from a suitable, optically transmissive polymeric material, such as, for example, acrylic polymers (e.g., polymethylmethacrylate (PMMA)).

Figure 5:
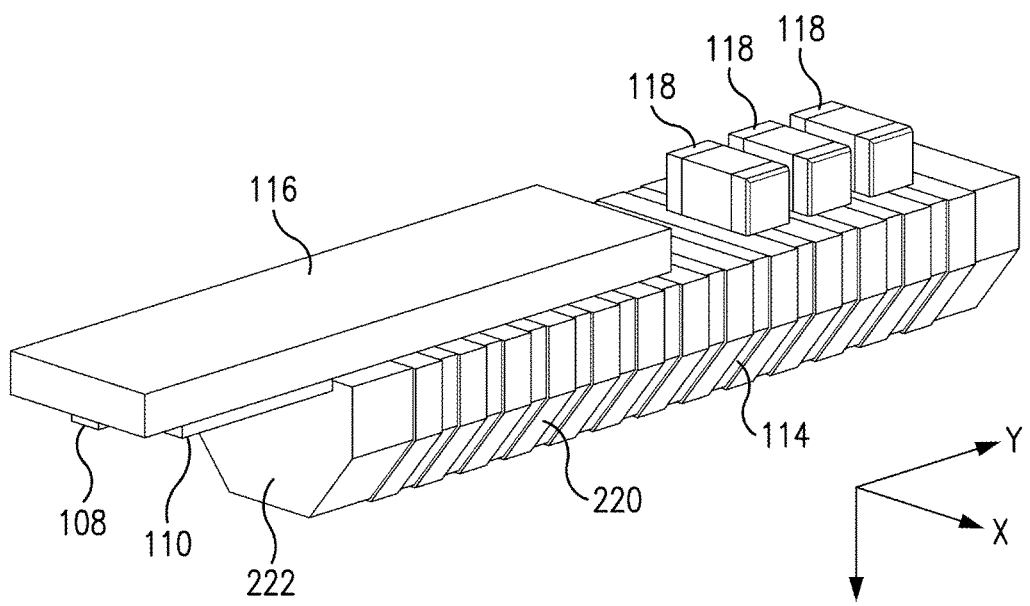
Figure 6:
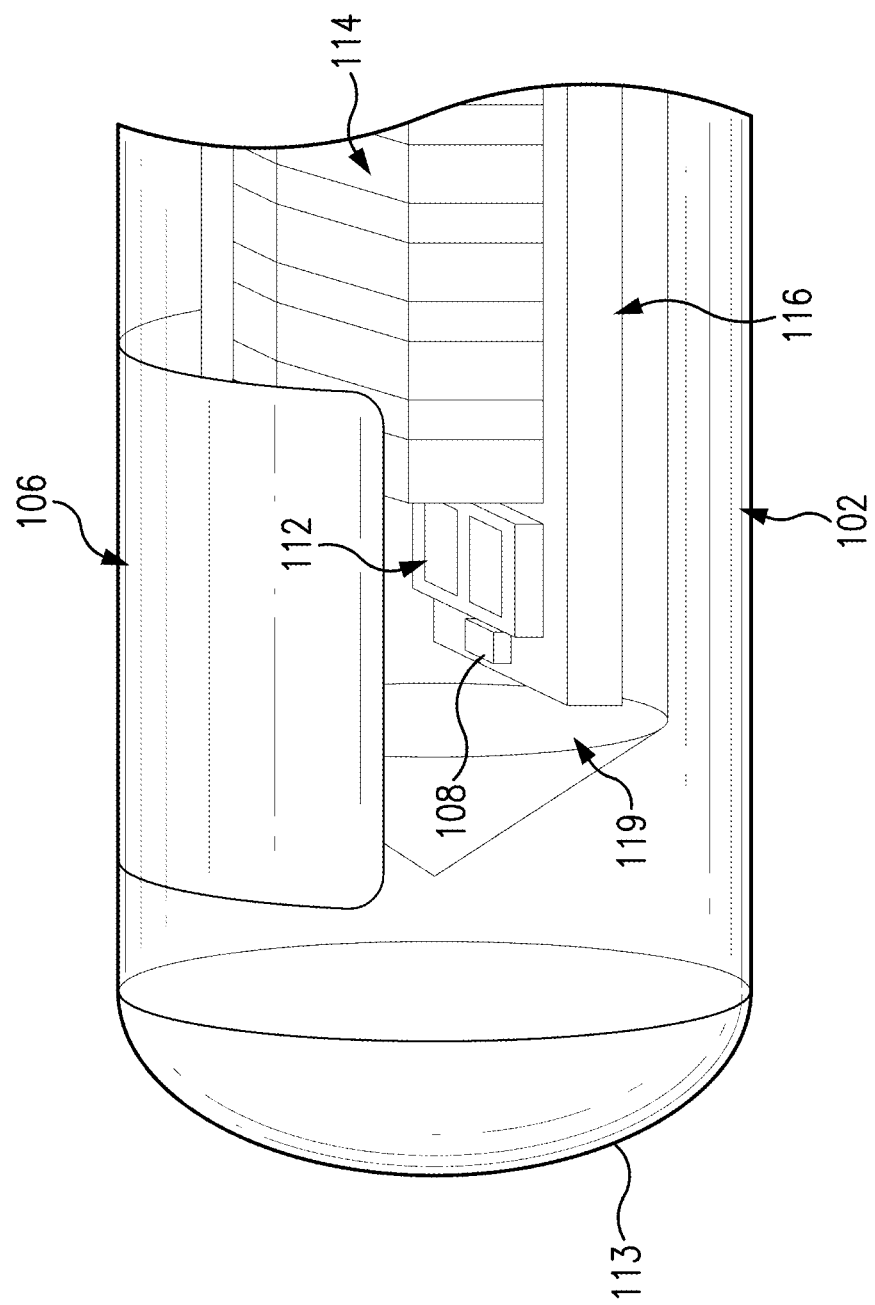
FIG. 6 illustrates a side view of a sensor embodying aspects of the present invention.
Figure 7:
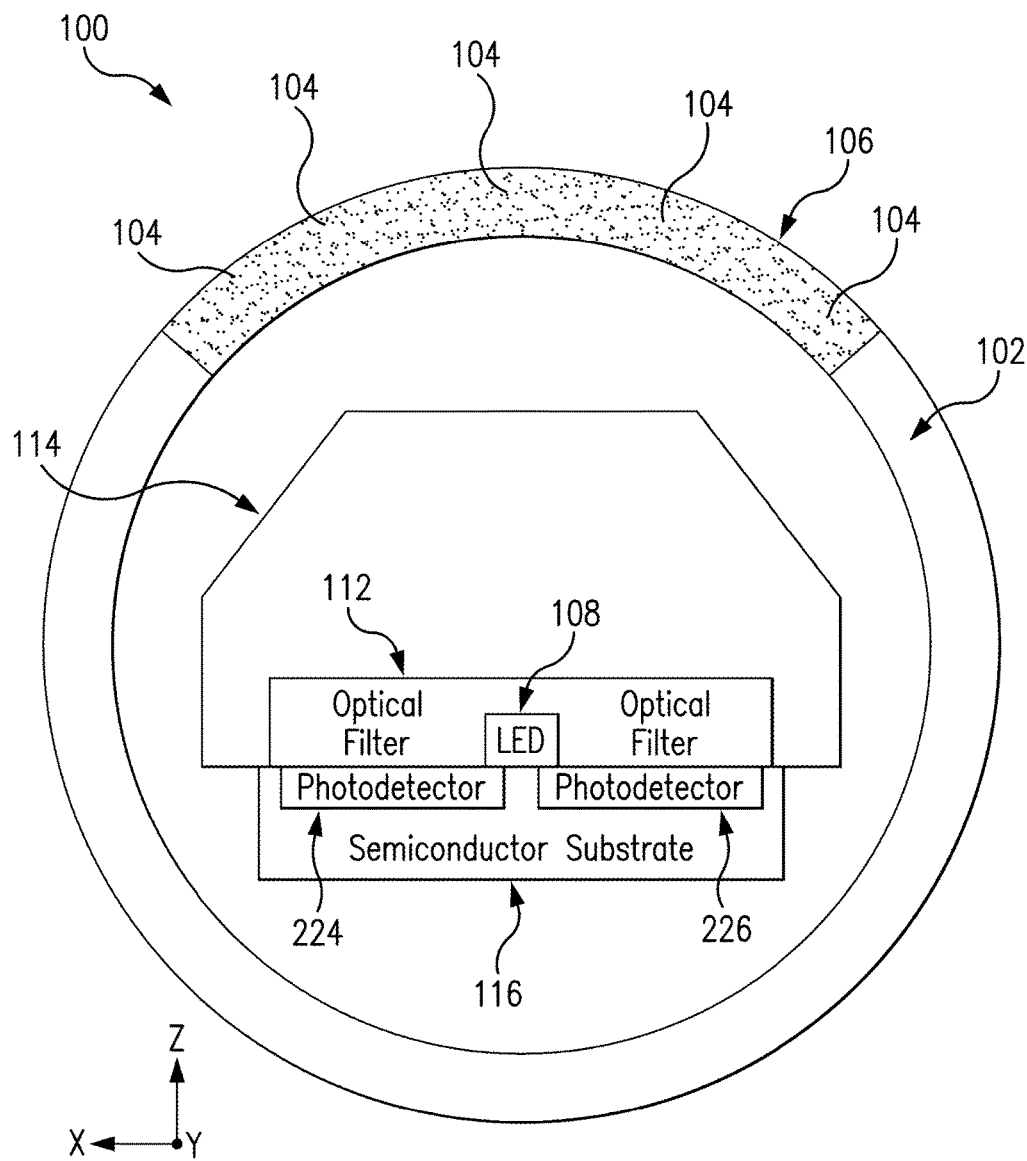
FIG. 7 illustrates a cross-sectional end view of a sensor embodying aspects of the present invention.
Figure 8:
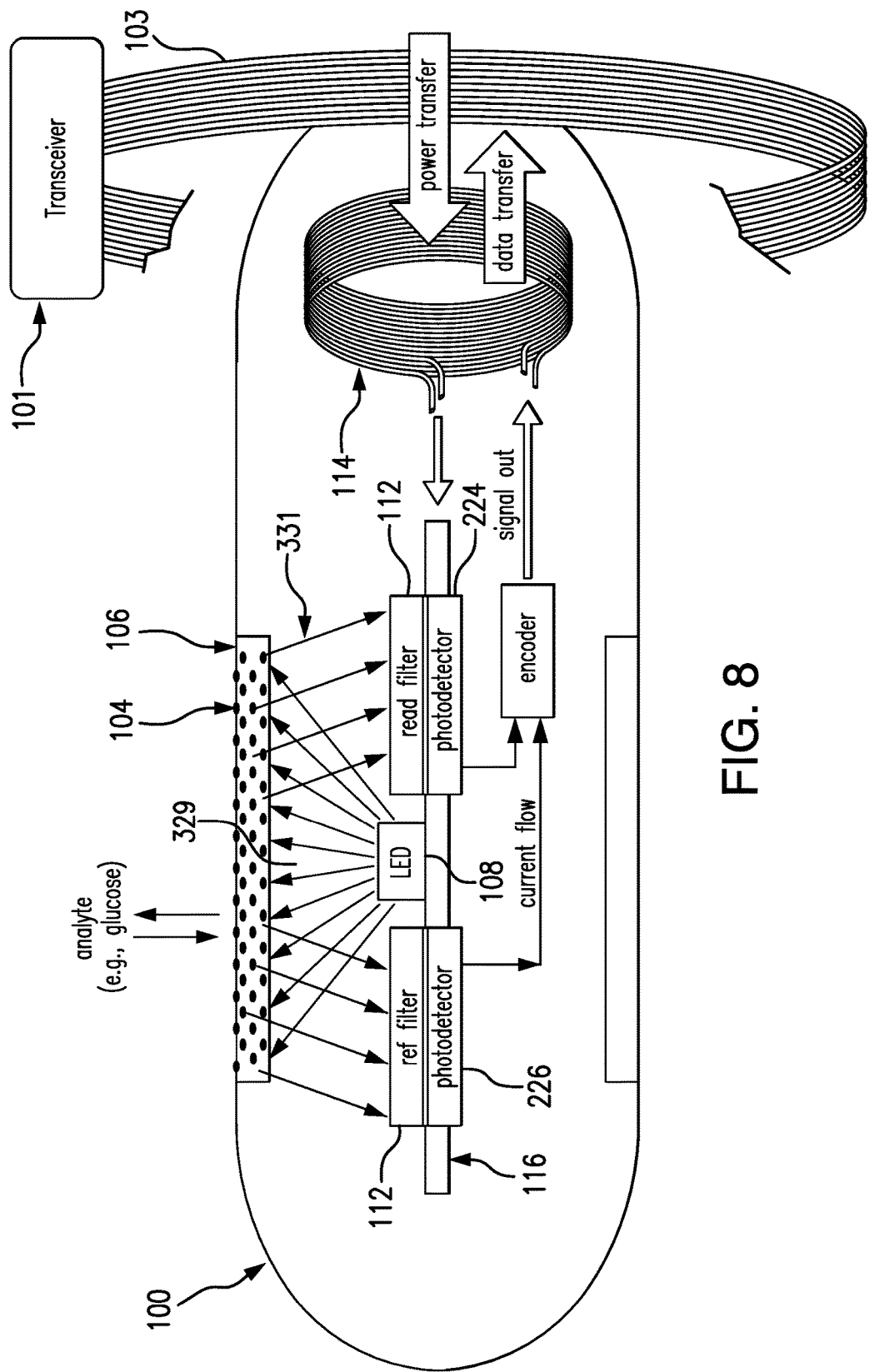
FIG. 8 illustrates a cross-sectional side view of a sensor in operation in accordance with an embodiment of the present invention.

In the embodiment illustrated in FIGS. 2-8, the sensor 100 includes indicator molecules 104 (see, e.g., FIGS. 7 and 8). Indicator molecules 104 may be fluorescent indicator molecules or absorption indicator molecules. In some non-limiting embodiments, the indicator molecules 104 may be as described in U.S. Pat. No. 6,344,360 or U.S. patent application Ser. No. 13/937,871, which are incorporated herein by reference in their entireties. In some non-limiting embodiments, sensor 100 may include an indicator element 106. In some non-limiting embodiments, the indicator element 106 may be a polymer graft (i.e., matrix layer or gel) coated or embedded on at least a portion of the exterior surface of the sensor housing 102, with the indicator molecules 104 distributed throughout the graft. The indicator element 106 may be embedded within the sensor housing 102 and/or cover the entire surface of sensor housing 102 or only one or more portions of the surface of housing 102. Similarly, the indicator molecules 104 may be distributed throughout the entire indicator element 106 or only throughout one or more portions of the indicator element 106.

In the illustrated embodiment, the sensor 100 includes a light source 108, which may be, for example, a light emitting diode (LED) or other light source that emits light over a range of wavelengths that interact with the indicator molecules 104.

In the illustrated embodiment, sensor 100 also includes one or more photodetectors 110 (e.g., photodiodes, phototransistors, photoresistors, or other photosensitive elements) which, in the case of a fluorescence-based sensor, is sensitive to fluorescent light emitted by the indicator molecules 104 such that a signal is generated by the photodetector 110 in response thereto that is indicative of the level of fluorescence of the indicator molecules and, thus, the amount of analyte of interest (e.g., glucose).

As illustrated in FIG. 8, some embodiments of sensor 100 include one or more optical filters 112, such as high pass or band pass filters, that may cover a photosensitive side of the one or more photodetectors 110.

As shown in FIG. 8, in some embodiments, sensor 100 may be wholly self-contained. In other words, the sensor may be constructed in such a way that no electrical leads extend into or out of the sensor housing 102 to supply power to the sensor (e.g., for driving the light source 108) or to convey signals from the sensor 100. Instead, in one embodiment, sensor 100 may be powered by an external power source (e.g., external transceiver 101). For example, the external power source may generate a magnetic field to induce a current in an inductive element 114 (e.g., a coil or other inductive element). Additionally, the sensor 100 may use the inductive element 114 to communicate information to an external sensor reader (e.g., transceiver 101). In some embodiments, the external power source and data reader may be the same device (e.g., transceiver 101). Although, in FIG. 8, antenna 103 of transceiver 101 is illustrated as a coil that wraps around the sensor 100, this is not required. In some alternative embodiments, the sensor may have a different configuration, such as, for example, those described in U.S. patent application Ser. No. 13/650,016, which is incorporated herein by reference in its entirety, with particular reference to FIGS. 2A-2C, or those described in U.S. patent application Ser. No. 13/937,871, which is incorporated herein by reference in its entirety.

In some embodiments, sensor 100 may include a semiconductor substrate 116 and circuitry may be fabricated in the semiconductor substrate 116. The circuitry may include analog and/or digital circuitry. In some embodiments, the circuitry may incorporate some or all of the structure described in U.S. patent application Ser. No. 13/650,016, which is incorporated herein by reference in its entirety, with particular reference to FIG. 11D. Also, although in some preferred embodiments the circuitry is fabricated in the semiconductor substrate 116, in alternative embodiments, a portion or all of the circuitry may be mounted or otherwise attached to the semiconductor substrate 116. In other words, in alternative embodiments, a portion or all of the circuitry may include discrete circuit elements, an integrated circuit (e.g., an application specific integrated circuit (ASIC)) and/or other electronic components discrete and may be secured to the semiconductor substrate 116, which may provide communication paths between the various secured components.

In some embodiments, the one or more photodetectors 110 may be mounted on the semiconductor substrate 116, but, in some preferred embodiments, the one or more photodetectors 110 may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

In some embodiments, the sensor 100 may include one or more capacitors 118. The one or more capacitors 118 may be, for example, one or more tuning capacitors and/or one or more regulation capacitors. Further, the one or more capacitors 118 may be in addition to one or more capacitors fabricated in the semiconductor substrate 116.

In some embodiments, the sensor 100 may include a reflector 119 (i.e., mirror). Reflector 119 may be attached to the semiconductor substrate 116 at an end thereof (see, FIG. 3). In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from reaching the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen toxins, pharmaceuticals or other drugs, hormones, and other metabolic analytes in, for example, the human body. The specific composition of the indicator element 106 and the indicator molecules 104 therein may vary depending on the particular analyte the sensor is to be used to detect and/or where the sensor is to be used to detect the analyte (i.e., in interstitial fluid). Preferably, however, indicator element 106 should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

Figure 4:
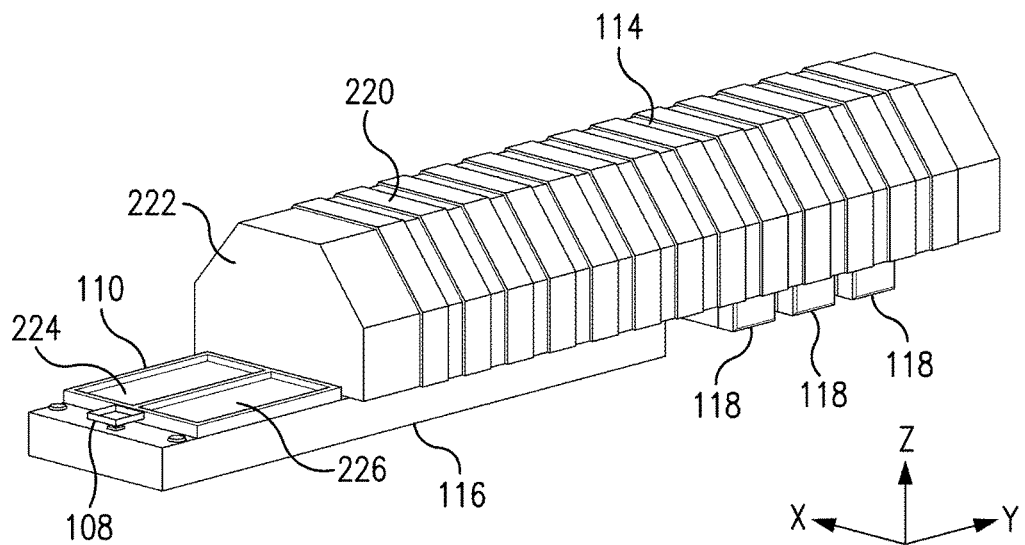
FIGS. 4 and 5 illustrate perspective views of sensor components within the sensor body/shell/capsule of a sensor embodying aspects of the present invention.

FIGS. 4 and 5 illustrate perspective views of the sensor 100. In FIGS. 4 and 5, the sensor housing 102, filters 112, and the reflector 119, which may be included in some embodiments of the sensor 100, are not illustrated. As shown in the illustrated embodiment, the inductive element 114 may comprise a coil 220. In one embodiment, coil 220 may be a copper coil but other conductive materials, such as, for example, screen printed gold, may alternatively be used. In some embodiments, the coil 220 is formed around a ferrite core 222. Although core 222 is ferrite in some embodiments, in other embodiments, other core materials may alternatively be used. In some embodiments, coil 220 is not formed around a core. Although coil 220 is illustrated as a cylindrical coil in FIGS. 4 and 5, in other embodiments, coil 220 may be a different type of coil, such as, for example, a flat coil.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein by reference in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which is important for implant applications, and increases cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the illustrated embodiment, the one or more photodetectors 110 include a first photodetector 224 and a second photodetector 226. First and second photodetectors 224 and 226 may be mounted on or fabricated in the semiconductor substrate 116.

FIGS. 6 and 7 illustrate side and cross-sectional views, respectively, of the sensor 100 according to one embodiment. As illustrated in FIGS. 6 and 7, the light source 108 may be positioned to emit light that travels within the sensor housing 102 and reaches the indicator molecules 104 of the indicator element 106, and the photodetectors 110, which may be located beneath filters 112, may be positioned to receive light from the indicator molecules 104 of the indicator element 106.

In operation, as shown in FIG. 8, the light source 108 (e.g., an LED) may emit excitation light 329 that travels within the sensor housing 102 and reaches the indicator molecules 104 of the indicator element 106. In a non-limiting embodiment, the excitation light 329 may cause the indicator molecules 104 distributed in indicator element 106 to fluoresce. As the indicator element 106 may be permeable to the analyte (e.g., glucose) in the medium (e.g., blood or interstitial fluid) into which the sensor 100 is implanted, the indicator molecules 104 in the indicator element 106 may interact with the analyte in the medium and, when irradiated by the excitation light 329, may emit indicator fluorescent light 331 indicative of the presence and/or concentration of the analyte in the medium.

Figure 3:
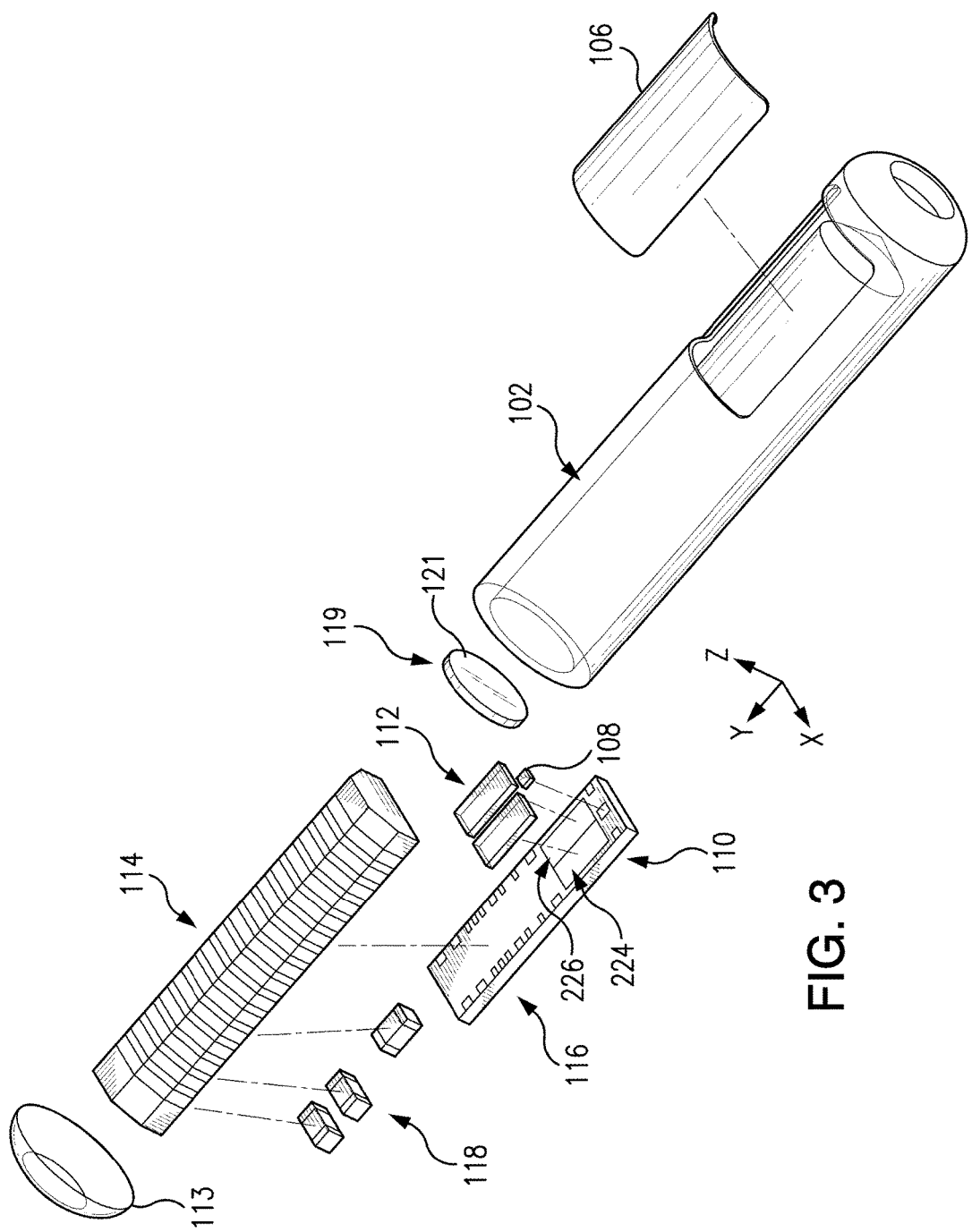
FIG. 3 illustrates an exploded view of a sensor embodying aspects of the present invention.

The photodetectors 224 and 226 are used to receive light (see FIG. 3). Each photodetector 224 and 226 may be covered by a filter 112 that allows only a certain subset of wavelengths of light to pass through (see FIG. 3). The filters 112 may be thin film (e.g., dichroic) filters deposited on glass, and the filters 112 may pass only a narrow band of wavelengths and otherwise reflect the received light. The filters 112 may be identical (e.g., both filters 112 may allow signal light to pass) or different (e.g., one filter 112 may allow signal light to pass, and the other filter 112 may allow reference light to pass).

Photodetector 226 may be a reference photodetector, and the filter 112 may pass light at the same wavelength as the wavelength of the excitation light 329 emitted from the light source 108 (e.g., 378 nm). Photodetector 224 may be a signal photodetector that detects the amount of fluoresced light 331 that is emitted from the indicator molecules 104 in the indicator element 106. In some non-limiting embodiments, the signal filter 112 (i.e., the filter 112 covering photodetector 224) may pass light in the range of about 400 nm to 500 nm. Higher analyte levels may correspond to a greater amount of fluorescence of the molecules 104 in the indicator element 106, and therefore, a greater amount of photons striking the signal photodetector 224.

Embodiments of the present invention may include one or more of several possible solutions to the light-blocking and/or indicator element deterioration problems described above.

Figure 9:
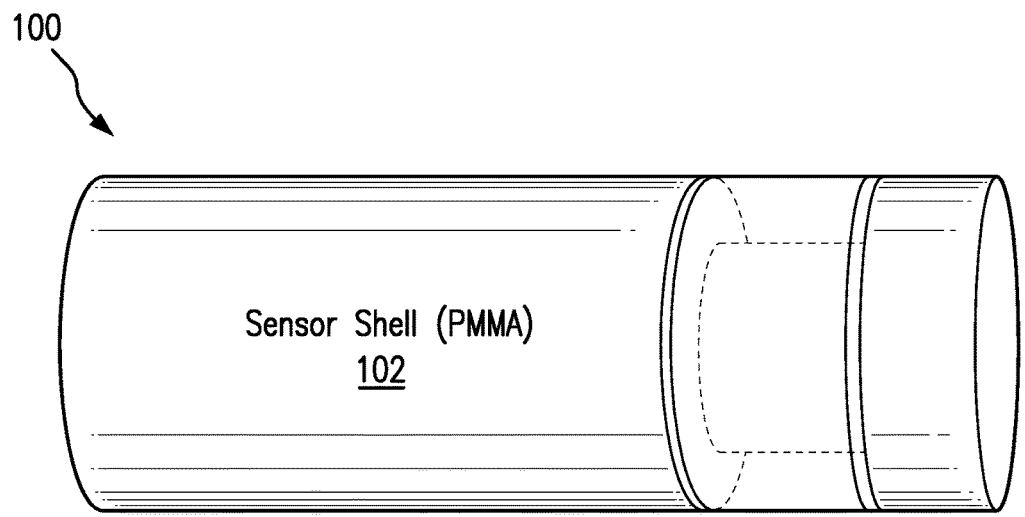
FIGS. 9 and 10 illustrate a side view of a sensor, without and with a membrane over the indicator element, respectively, in accordance with an embodiment of the present invention.
Figure 10:
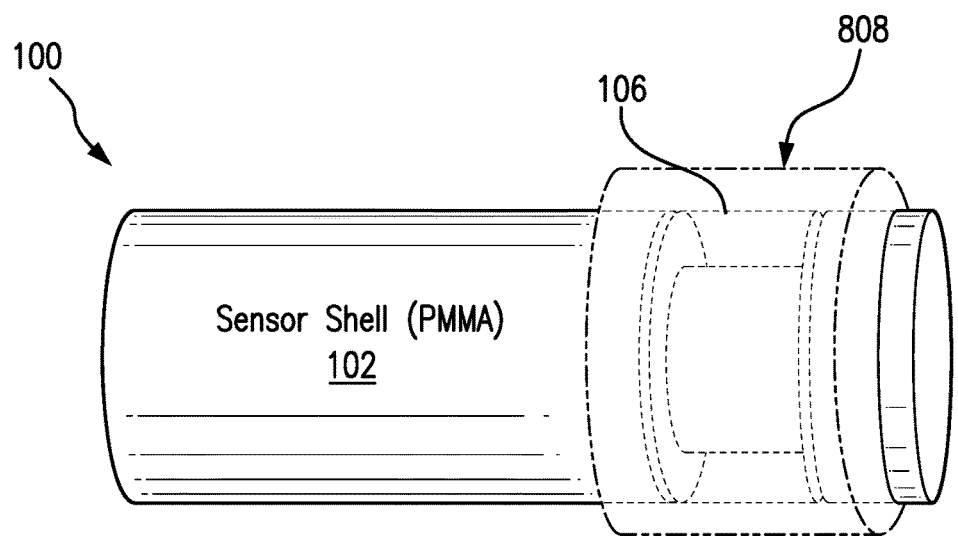

FIGS. 9 and 10 illustrate a sensor 100 having a membrane 808 in accordance with an embodiment of the present invention. FIG. 9 shows the sensor 100 without the membrane 808, and FIG. 10 shows the sensor 100 with the membrane 808. In some non-limiting embodiments, the sensor 100 may have a sensor housing/shell 102 and an indicator element 106 embedded within and/or covering at least a portion of the housing 102. The indicator element 106 may include indicator molecules 104.

In regard to indicator element deterioration, as explained above, white blood cells, including neutrophils, may attack an implanted sensor 100. The neutrophils release, inter alia, hydrogen peroxide, which may degrade indicator molecules 104 (e.g., by oxidizing a boronate group of an indicator molecule and disabling the ability of the indicator molecule to bind glucose).

As illustrated in FIGS. 9 and 10, in some non-limiting embodiments, the indicator element 106 may a have thin layer (e.g., 10 nm) on the outside of the indicator element 106. The thin layer may protect against indicator molecule degradation. The thin layer may be platinum, and the platinum may be sputtered onto the outside surface of the indicator element 106, which includes the indicator molecules 104. Platinum rapidly catalyzes the conversion of hydrogen peroxide into water and oxygen, which are harmless to the sensor. The rate of this reaction is much faster than the boronate oxidation; thus, the platinum provides some protection against oxidation by reactive oxygen species. Although platinum is the catalyst of the conversion of hydrogen peroxide into water and oxygen in some embodiments, in alternative embodiments, other catalysts of this reaction, such as, for example, palladium or catalase, may be used for the thin layer instead of or in addition to platinum.

As illustrated in FIG. 10, the sensor 100 may have a membrane 808 over the indicator element 106 (and over any thin layer/film on the outside of the indicator element 106).

The membrane 808 may be opaque and, therefore, perform a light-blocking function. In other words, the opaque nature of the membrane may serve the function of effectively blocking extraneous light. In some non-limiting embodiments, only the opaque membrane 808 is used to block light, and, in these embodiments, the sensor 100 does not include an additional layer, such as the layer 810 illustrated in FIG. 11, over the membrane 808. However, in other embodiments, the sensor 100 may include both a membrane 808 that is opaque and an additional layer, such as layer 810 illustrated in FIG. 11, over the membrane 808.

In some non-limiting embodiments, the opaque membrane 808 may be physically attached over the indicator element 106 after boring an additional, smaller well into the capsule/housing 102. In some non-limiting embodiments, the membrane 808 may be made of a mesh material, such as, for example, as a woven, non-woven, sintered, precipitated, or electrospun nylon. However, this is not required, and, in some alternative embodiments, the membrane 808 may be made of another material, such as, for example, cellulose acetate, polytetrafluoroethylene, polyethylene teraphthlate, polypropylene, polyvinyl alcohol, polybutylene terephthalate, polyether ether ketone, polyanhydride, polyamide, polyvinylchloride, polyethersulfone, polyvinylidene difluoride, polycarbonate, or derivatives thereof.

In some embodiments, the membrane 808 may be porous. In other words, the membrane 808 may be structured so that it channels one or more analytes (e.g., glucose) to the indicator element 106. For example, in one non-limiting embodiment, the membrane 808 has small pores (e.g., pores having a pore size of microns or less) that block the passage of white blood cells (e.g., neutrophils), which are between 6 and 12 microns in diameter, from reaching the underlying indicator element 106 to attack it. The small pores, however, would at the same time be large enough to allow the analyte to reach the indicator element 106. In this way, a porous membrane 808 having small pores would increase sensor longevity while not affecting the ability of the sensor 100 to measure the concentration of an analyte. In some non-limiting embodiments, the pores formed through the membrane 808 may have a size of 0.45-6 microns. In some embodiments, polymers that control or reduce the body's response to an implant (i.e., the foreign body response) such as polyethylene oxides (PEO), hydroxy acrylates (HEMA), or fluoropolymers could be coated onto any of the membranes 808 (e.g., polytetrafluoroethylene (PTFE) coated onto polyethylene teraphthlate (PET) or PEO coated onto nylon).

In some embodiments, the opaque membrane 808 may be made from a material that does not react adversely to the body's defenses. In non-limiting embodiments, the material from which the opaque membrane 808 is made may additionally be both porous (e.g., to allow and analyte, such as glucose, to flow through it) and opaque (e.g., to prevent light from traveling through it). For example, in some embodiments, the membrane material may be a hydrophilic material, such as, for example, nylon or cellulose acetate. In other embodiments, the membrane material may be a hydrophobic material, such as, for example, polyethylene terephthalate or polytetrafluoroethylene.

Figure 11:
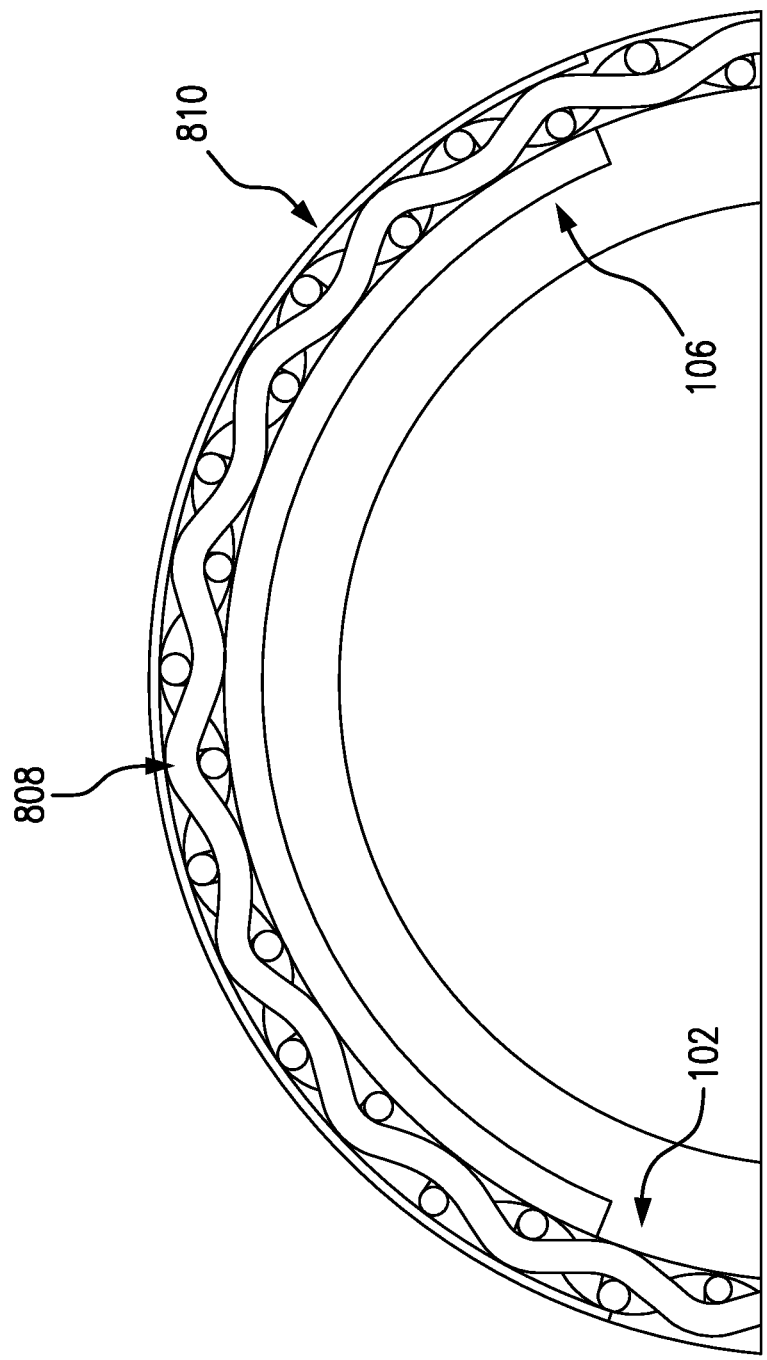
FIGS. 11 and 12 illustrate a cross-sectional view of a sensor in accordance with an embodiment of the present invention.
Figure 12:
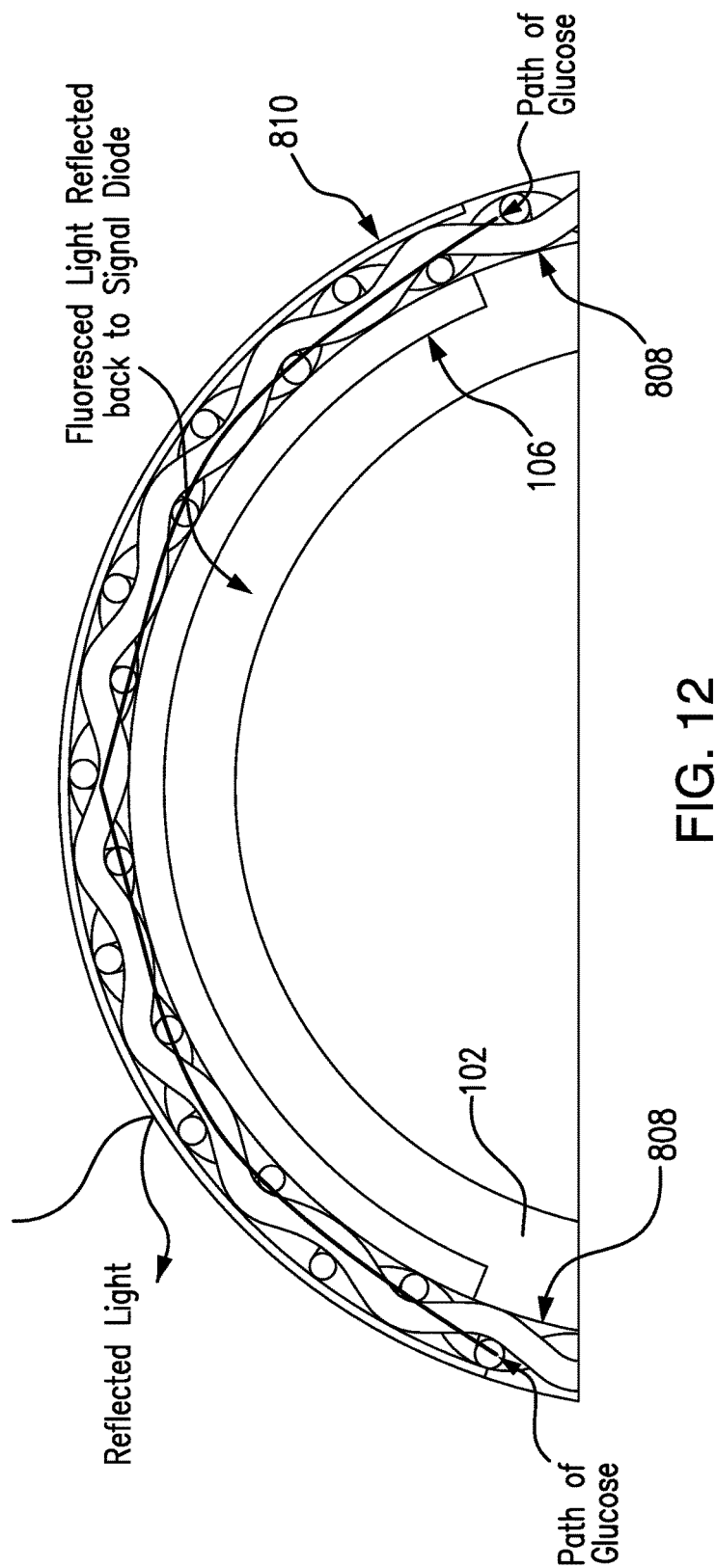

FIGS. 11 and 12 illustrate a cross-sectional view of a sensor 100 having a membrane 808 in accordance with another embodiment of the present invention. As illustrated in FIGS. 11 and 12, the indicator element 106 of sensor 100 may be covered by a membrane 808, and the sensor 100 may additionally include a thin layer 810, which may also block light. For example, in some embodiments, the layer 810 may prevent excitation light 329 from the light source 108 from escaping the sensor housing/capsule 102 and prevent undesirable light entering the sensor housing/capsule 102. This undesirable light may be from outside the body and/or may be reflected or fluoresced excitation light being returned from body tissue. Reduction of each type of undesirable light would improve sensor accuracy. In one non-limiting embodiment, the layer 810 may be a mirror. In one non-limiting embodiment, an additional smaller well may be bored into the capsule/housing 102, a membrane 108 may be physically attached over the indicator element 106, and an additional blocking layer 810 may then be attached.

In some embodiments, the membrane 808 may channel an analyte to the indicator element 106, while the layer 810 and/or membrane 808 simultaneously block any errant light.

The membrane 808 may be porous such that it does not physically block the analyte (e.g., glucose) from reaching the indicator element 106. Furthermore, the membrane 808 may have channels small enough to block white blood cells from reaching the indicator element 106, but large enough to allow for the passage of red blood cells and glucose molecules.

In some non-limiting embodiments, the layer 810 may be a material that does not adversely react to the body's defenses. In one non-limiting embodiment, platinum may serve as both the material for the membrane 808 and as the material for the layer 810 because platinum catalyzes hydrogen peroxide species and reduces the deterioration of the indicator element 106 that would otherwise occur, while also blocking extraneous light from over stimulating the indicator element 106. With a platinum membrane 808 in place, hydrogen peroxide, which is produced by a patient's white blood cells through the disproportionation of superoxide ($O_2^-$), would quickly be catalyzed to water and oxygen, which are harmless to the transceiver 101. Thus, a platinum membrane 808 may increase the lifetime of the sensor 100 in the body.

In some alternative embodiments, polymers, such as, for example, nylon, cellulose acetate, polytetrafluoroethylene (PTFE), polyethylene teraphthlate (PET), polypropylene (PP), polyvinyl alcohol (PVA), polybutylene terephthalate (PBT), polyether ether ketone (PEEK), polyanhydride, polyamide, polyvinylchloride (PVC), polyethersulfone (PES), polyvinylidene difluoride (PVDF), or polycarbonate may additionally or alternatively be used as the membrane material.

Platinum may not, however, offer complete protection from the in vivo oxidation in all cases.

Figure 13:
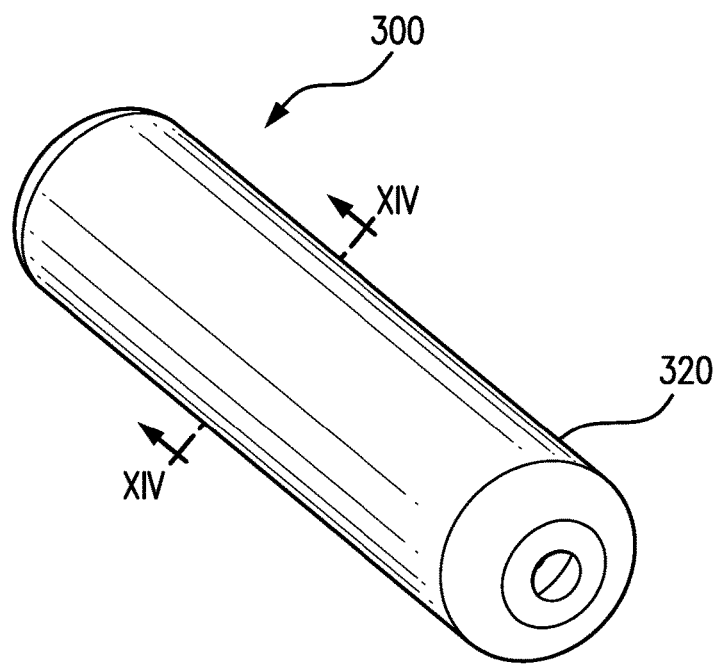
FIG. 13 is a perspective view of an alternate embodiment of a sensor embodying aspects of the present invention and comprising an opaque diffusion membrane substantially, or totally, covering the housing of a sensor.

An alternative solution to the light blocking and immune response issues is an opaque diffusion membrane that is configured to both block light from entering or exiting the sensor housing and prevent reactive oxygen species-generating cells from direct tissue contact with the indicator element. A sensor assembly embodying aspects of the invention of this alternative solution is represented by reference number 300 in FIG. 13, which is a perspective view of the sensor assembly. Sensor assembly 300 comprises an implantable sensor, such as sensor 100 described above, covered or substantially covered by an opaque diffusion membrane 320.

Figure 14:
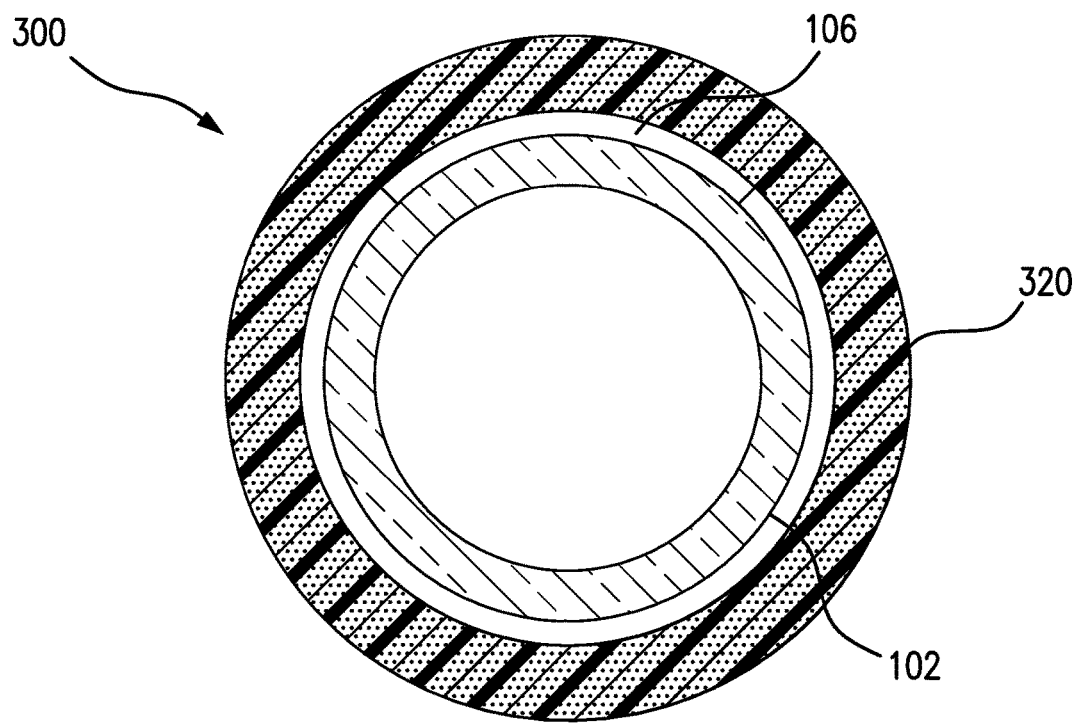
FIG. 14 is a transverse cross-section of the sensor and opaque diffusion membrane along the line XIV-XIV in FIG. 13.

FIG. 14 is a transverse cross-section of the sensor assembly 300. For simplicity of the figure, the internal components of the sensor, such as the light source, filters, antennae, etc., are not shown in FIG. 14. The sensor assembly 300 may comprise a sensor housing 102 which, as described above, may comprise a suitable, optically transmissive polymer material, such as PMMA. Further, as described above, the sensor may include an indicator element 106 coated on or embedded in at least a portion of the exterior surface of the housing 102. The diffusion membrane 320 is disposed over the sensor housing 102 and indicator element 106. It should be noted that the relative thicknesses of the various layers of the sensor assembly 300 shown in FIG. 14 are for clarity of illustration and should not be viewed as limiting.

Preferably, the diffusion membrane 320 is made of a material that does not react adversely to the body's defenses but can also be effectively manipulated to be both porous to allow an analyte (e.g., glucose) to flow through the membrane and opaque to substantially prevent light transmission through the membrane. Suitable materials include, for example, nylon or cellulose acetate because such materials are hydrophilic and can therefore be expected to allow an analyte solution (e.g., a glucose solution) to pass through pores formed in the material. Ready passage of the analyte solution through the membrane pores will facilitate analyte readings with less of a time lag. In addition, porous membranes formed from hydrophobic materials, such as polypropylene, polyethylene terephthalate ("PET"), and polytetrafluoroethylene("PTFE"), can be made hydrophilic by known surface treatments methods, such as oxygen plasma treatment or chemical treatments to generate hydrophilic surface moieties or by grafting of hydrophilic polymers onto the surface of hydrophobic materials, and thus allow facile diffusion of analyte solutions.

One example of an opaque diffusion membrane embodying aspects of the invention may comprise a porous PET tube loaded with an opaque colorant (e.g., TiO2, carbon black). The total amount of colorant added to the PET may be altered such that no measurable light transmission through the diffusion membrane can be detected at the wavelengths of interest. For example, the amount of colorant added to the diffusion membrane material may be increased to a point at which no measurable light is transmitted through the PET (or other membrane material) layer.

Preferably, in one embodiment, the opaque diffusion membrane 320 extends over the entire sensor housing 102 covering substantially any and all light paths into or out of the sensor housing. Preferably, the membrane would include end covers with or without wrapped ends.

A goal is to match light-blocking ability of the membrane 320 with the porosity of the membrane material. Accordingly, the percent open area of the membrane material is preferably sufficiently small (e.g., 6-25%) to block light, but still has sufficient porosity to allow diffusion. In one exemplary embodiment, PET membrane material could be tracked, etched, or laser drilled to add pores. In some non-limiting embodiments, the pores added to the PET membrane material may have a size at the exit that prevents leukocytes (white blood cells), which have a size of approximately 7-80 microns, from passing through the pores. For example, in one non-limiting embodiment, the pores may have a size of approximately 5-7 microns at the exit. For another example, in some non-limiting embodiments, the pores formed through the membrane 320 may have a size of 0.45-6 microns.

Another important characteristic of the diffusion membrane 320 is to provide maximum distance between the white blood cells and the indicator element 106. Thus, in one embodiment of a diffusion membrane 320 embodying aspects of the invention, the membrane 320 comprises a PET layer having a thickness of approximately 25 to 50 microns to keep immune cells (e.g., white blood cells) at a sufficient distance away from the indicator element 106.

Figure 15:
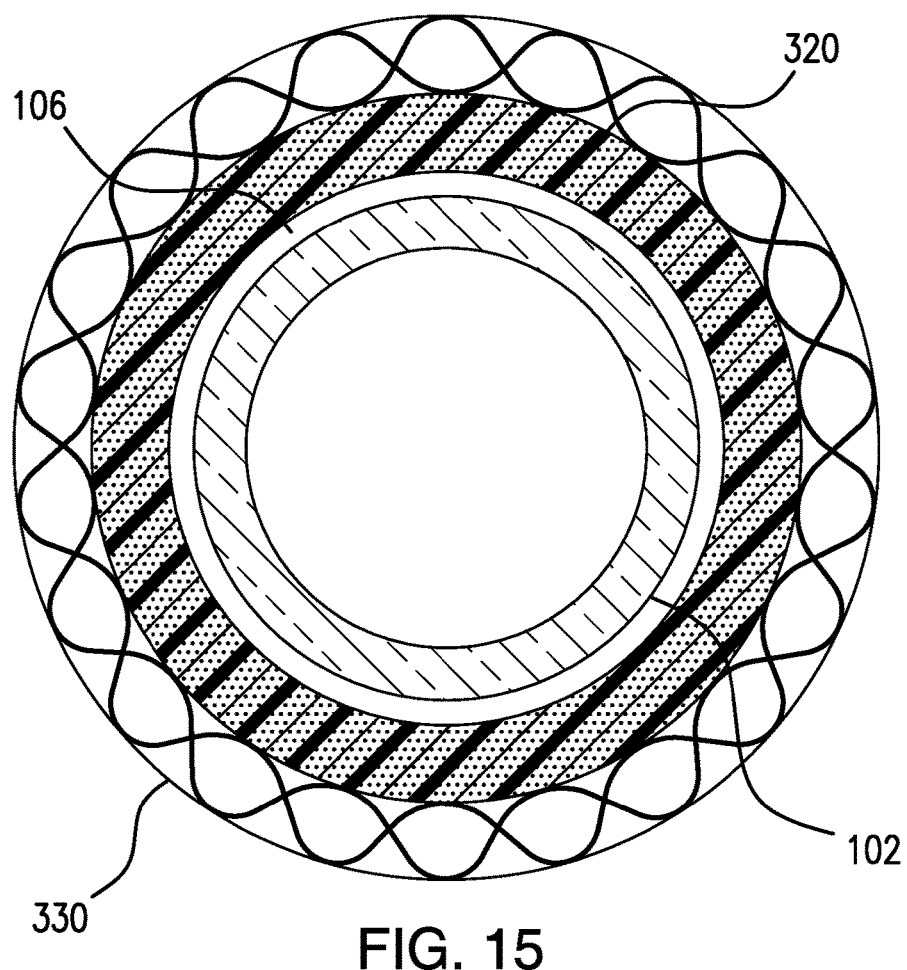
FIG. 15 is an alternate embodiment of a sensor covered with an opaque diffusion membrane.

As shown in FIG. 15, another embodiment of a diffusion membrane embodying aspects of the invention is configured to maintain a sufficient distance between white blood cells and the indicator element 106 and employs a combination of materials comprising a relatively thick (e.g., 50-200 micron) porous, torturous path material 330 disposed either beneath or on top of the porous PET (or other material) layer 320 to provide an additional optically isolating layer and to further increase the distance between the immune cell (e.g., white blood cells) and the indicator element 106. A suitable material for the torturous path layer includes nylon. The torturous path material 330 provides a longer path through which ROS produced by the white blood cells would need to travel before reaching analyte-sensing indicator element 106 and thereby increases the degree to which the ROS are diluted and/or degraded. Accordingly, the tortuous path material 330 enhances the white blood cell-blocking capability of such a multi-layer diffusion membrane comprising layers 320 and 330.

In some embodiments, the sensor 100 may include a plurality of membranes. For example, in some non-limiting embodiments, the sensor 100 may include one or more catalytic membranes, one or more porous immune response blocking membranes, and/or one or more light blocking membranes. In one non-limiting embodiment, the sensor 100 may include a catalytic membrane on top of the indicator element 106, a porous immune response blocking membrane on top of the catalytic membrane, and a light blocking membrane on top of the porous immune response blocking membrane. In another non-limiting embodiment, the membranes may be arranged over the indicator element 106 in a different order. In yet another non-limiting embodiment, one or more of the plurality of membranes may have one or more functions (e.g., a sensor 100 may include membrane having catalytic membrane and a membrane that blocks both light and immune response).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, in some embodiments, the sensor 100 is a subcutaneous electrooptical sensor, but this is not required, and, in other embodiments, the sensor 100 may be a transcutaneous and/or electrochemical sensor. Also, circuitry of the sensor 100 and reader 101 may be implemented in hardware, software, or a combination of hardware and software. The software may be implemented as computer executable instructions that, when executed by a processor, cause the processor to perform one or more functions.

What is claimed is:

1. A sensor for in vivo detection of the presence, amount, and/or concentration of an analyte in a medium within a living animal, the sensor comprising:
   a sensor housing;
   an indicator element embedded within and/or covering at least a portion of the sensor housing;
   a membrane over at least a portion of the indicator, wherein the membrane has pores configured to substantially prevent white blood cells from passing through the membrane but to permit the analyte to pass through the membrane, and pores formed through the membrane have a size of 0.45-6 microns; and
   a layer over the membrane, wherein the layer is configured to block (i) external light from reaching the indicator element and (ii) light from the sensor housing that has passed through the indicator element from reaching bodily tissue of the living animal.

2. The sensor of claim 1, wherein the analyte is glucose.

3. The sensor of claim 1, wherein the membrane is opaque.

4. The sensor of claim 1, wherein the membrane reduces deterioration of the indicator element by catalyzing degradation of reactive oxygen species (ROS).

5. The sensor of claim 4, wherein the layer reduces deterioration of the indicator element by catalyzing degradation of ROS.

6. The sensor of claim 1, further comprising a layer between the indicator element and the membrane.

7. The sensor of claim 6, wherein the layer between the indicator element and the membrane is a thin layer sputtered on the outside of the indicator element.

8. The sensor of claim 1, wherein the membrane is wrapped around the indicator element.

9. The sensor of claim 1, wherein the layer is a mirror.

10. The sensor of claim 1, wherein the layer reduces deterioration of the indicator element by catalyzing degradation of reactive oxygen species (ROS).

11. The sensor of claim 1, wherein the membrane comprises platinum, and the layer comprises platinum.

12. The sensor of claim 1, wherein the membrane comprises a mesh material.

13. The sensor of claim 1, wherein the membrane comprises a layer of material selected from the group consisting of nylon, cellulose acetate, polytetrafluoroethylene, polyethylene teraphthlate, polypropylene, polyvinyl alcohol, polybutylene terephthalate, polyether ether ketone, polyanhydride, polyamide, polyvinylchloride, polyethersulfone, polyethylene terephthalate, polyvinylidene difluoride, polytetrafluoroethylene, nitrocellulose, acrylate, poly(methyl methacrylate), polyacrylate homo- or copolymers, polycarbonate, derivatives thereof, and combinations thereof.

14. A sensor for in vivo detection of the presence, amount, and/or concentration of an analyte in a medium within a living animal, the sensor comprising:
a sensor housing;
an indicator element embedded within and/or covering at least a portion of the sensor housing; and
a porous, opaque diffusion membrane covering at least a portion of the sensor housing and a portion of the indicator element, wherein the diffusion membrane is configured to substantially prevent white blood cells from passing through the diffusion membrane and permit an analyte of interest to pass through the diffusion membrane to the indicator element and to substantially prevent transmission of light of at least a specified wavelength or range of wavelengths through the diffusion membrane, pores formed through the diffusion membrane have a size of 0.45-6 microns, and the diffusion membrane comprises an opaque or light absorbing colorant.

15. The sensor of claim 14, wherein the opaque or light absorbing colorant comprises $TiO_2$ or carbon black.

16. The sensor of claim 14, further comprising a layer.

17. The sensor of claim 16, wherein the layer comprises platinum.

18. The sensor of claim 16, wherein the layer is between the indicator element and the diffusion membrane.

19. The sensor of claim 18, wherein the layer is a thin layer sputtered on the outside of the indicator element.

20. The sensor of claim 14, wherein the indicator element is a polymer graft including indicator molecules.

21. The sensor of claim 14, wherein the diffusion membrane has a porosity of 3-60%.

22. The sensor of claim 14, wherein the hydrophilic layer has a thickness of 10-200 microns.

23. The sensor of claim 14, wherein the diffusion membrane comprises a layer of material selected from the group consisting of nylon, cellulose acetate, polytetrafluoroethylene, polyethylene teraphthlate, polypropylene, polyvinyl alcohol, polybutylene terephthalate, polyether ether ketone, polyanhydride, polyamide, polyvinylchloride, polyethersulfone, polyethylene terephthalate, polyvinylidene difluoride, polytetrafluoroethylene, nitrocellulose, acrylate, poly (methyl methacrylate), polyacrylate homo- or copolymers, polycarbonate, derivatives thereof, and combinations thereof.

24. The sensor of claim 14, wherein the diffusion membrane has a thickness of 10-200 microns.

25. The sensor of claim 14, wherein the analyte is glucose.

\* \* \* \* \*